United States Patent
Ogawa

(10) Patent No.: US 7,237,895 B2
(45) Date of Patent: Jul. 3, 2007

(54) OPHTHALMOLOGIC APPARATUS

(75) Inventor: Tetsuji Ogawa, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 978 days.

(21) Appl. No.: 10/606,247

(22) Filed: Jun. 26, 2003

(65) Prior Publication Data

US 2004/0008322 A1 Jan. 15, 2004

(30) Foreign Application Priority Data

Jul. 12, 2002 (JP) .............................. 2002-203753

(51) Int. Cl.
*A61B 3/14* (2006.01)
*A61B 3/10* (2006.01)
(52) U.S. Cl. ...................... 351/208; 351/204
(58) Field of Classification Search ............... 351/204, 351/206, 208
See application file for complete search history.

(56) References Cited

U.S. PATENT DOCUMENTS

| 5,042,484 A | 8/1991 | Hideshima |
| 5,532,769 A | 7/1996 | Miwa et al. |
| 5,680,196 A * | 10/1997 | Masuda ...................... 351/208 |
| 2002/0089643 A1 | 7/2002 | Ogawa ........................ 351/206 |

FOREIGN PATENT DOCUMENTS

| JP | 63-283620 | 11/1988 |
| JP | 2-252439 | 10/1990 |
| JP | 8-10225 | 1/1996 |
| JP | 8-117188 | 5/1996 |
| JP | 9-224912 | 9/1997 |
| JP | 10-328141 | 12/1998 |
| JP | 2002-566 | 1/2002 |

* cited by examiner

*Primary Examiner*—Ricky Mack
*Assistant Examiner*—William Choi
(74) *Attorney, Agent, or Firm*—Fitzpatrick, Cella, Harper & Scinto

(57) ABSTRACT

An ophthalmologic apparatus includes alignment driving means for aligning an examinee's eye, detecting means for detecting an alignment state of the examinee's eye, and alignment controlling means for controlling the alignment driving means based on the result detected by the detecting means. The alignment controlling means includes determining means for determining a quality of the result detected by the detecting means and counting means for counting outputs from the determining means within a predetermined period of time. The alignment controlling means performs interruption processing or warning processing of the alignment control based on the output of the counting means.

8 Claims, 3 Drawing Sheets

OPHTHALMOLOGIC APPARATUS

BACKGROUND OF THE INVENTION

1. Field of the Invention

The present invention relates to an ophthalmologic apparatus such as an ophthalmologic measuring apparatus for measuring intraocular pressure, refracting power, a corneal shape, and the like of an examinee's eye, and an ophthalmologic image-pickup apparatus for filming a predetermined region of an examinee's eye.

2. Description of the Related Art

Alignment operations for aligning an optical system specific to an ophthalmologic apparatus with a predetermined optimum position of an examinee's eye have been known. Recently, an ophthalmologic apparatus has been developed having an auto-alignment mechanism for automatically performing the alignment by combining various image analyses and indexing analyses with a driving means of an optical unit including the optical system. In the auto-alignment mechanism, there is one system where alignment control is continued until alignment is completed, while a method is disclosed in Japanese Patent Laid-Open No.8-117188 in that if the alignment is not completed within a predetermined period of time, the alignment is canceled by determining it as alignment failure. There is also a method disclosed in Japanese Patent Laid-Open No.10-328141 that provides a switch for stopping transition to the measurement operation even though the alignment is completed.

As a drawback in an auto-alignment device, automatic alignment performed by the device on an examinee's eye inspires terror to many examinees. Numerous examinees are especially frightened of a non-contact ophthalmotonometer, in which the distance between an eye and an objective lens is small and air is sprayed further into the eye.

Such an examinee requires patient assistance, such as fixing the examinee's head position or raising the examinee's eyelid by an operator such as a doctor.

However, in conventional auto-alignment systems mentioned above, the alignment control is continued on a frightened examinee, causing great pain to the examinee. Even when a time-out function is added as disclosed in Japanese Patent Laid-Open No.8-117188, the control is absolutely continued until the time-out, so that although the pain of an examinee is reduced, the problem is unsolved. Also, even in the case disclosed in Japanese Patent Laid-Open No.10-328141 where the measurement initiation after the alignment completion is controlled with a switch, the alignment control is continued so as to similarly inflict pain on the examinee, and furthermore, since an operator is asked to operate the switch, this is also a burden on the operator.

SUMMARY OF THE INVENTION

It is a first object of the present invention to provide an ophthalmologic apparatus that quantitatively determines whether an examinee is fearful at an earlier stage. The burden of the examinee is thereby minimized by interruption of the auto-alignment control or by giving the examinee a cautionary warning. This arrangement enables a patient care operation to be demanded in exact timing.

It is a second object of the present invention to provide an ophthalmologic apparatus with excellent operability capable of automatically restarting the auto-alignment control by determining that the normal patient care operation has been performed.

In order to achieve the above first object, an ophthalmologic apparatus according to the present invention comprises alignment driving means for aligning an examinee's eye; detecting means for detecting an alignment state of the examinee's eye; and alignment controlling means for controlling the alignment driving means based on a result detected by the detecting means, wherein the alignment controlling means comprises determining means for determining a quality of the detected result and counting means for counting outputs from the determining means within a predetermined period of time, and the alignment controlling means performs the control of the alignment driving means based on the output of the counting means.

In order to achieve the above second object, an ophthalmologic apparatus according to the present invention comprises alignment driving means for aligning an examinee's eye; detecting means for detecting an alignment state of the examinee's eye; and alignment controlling means for controlling the alignment driving means based on a result detected by the detecting means, wherein the alignment controlling means comprises determining means for determining a quality of the detected result and counting means for counting outputs from the determining means within a predetermined period of time, and the alignment controlling means performs interruption processing for interrupting the alignment control and restart processing for restarting the alignment control based on the output of the counting means.

As described above, an ophthalmologic apparatus according to the present invention determines whether an examinee is experiencing excessive fear in earlier stages by quantitatively determining the state of an examinee's eye so that the load of the examinee can be suppressed to a minimum by interrupting the auto-alignment control. Preferably, the ophthalmologic apparatus according to the present invention further requires an operator to perform a patient care operation at the precise time needed by issuing a warning. Additionally, the ophthalmologic apparatus according to the present invention automatically restarts the auto-alignment control by suppressing the load of the examinee to a minimum and determining whether the patient-care operation may be normally performed. The ophthalmologic apparatus performs the auto-alignment control by requiring the operator to perform a patient care operation at the precise time needed and also by precisely determining the initiation of the patient-care operation.

Further objects, features and advantages of the present invention will become apparent from the following description of the preferred embodiments with reference to the attached drawings.

DESCRIPTION OF THE PREFERRED EMBODIMENTS

Figure 1:
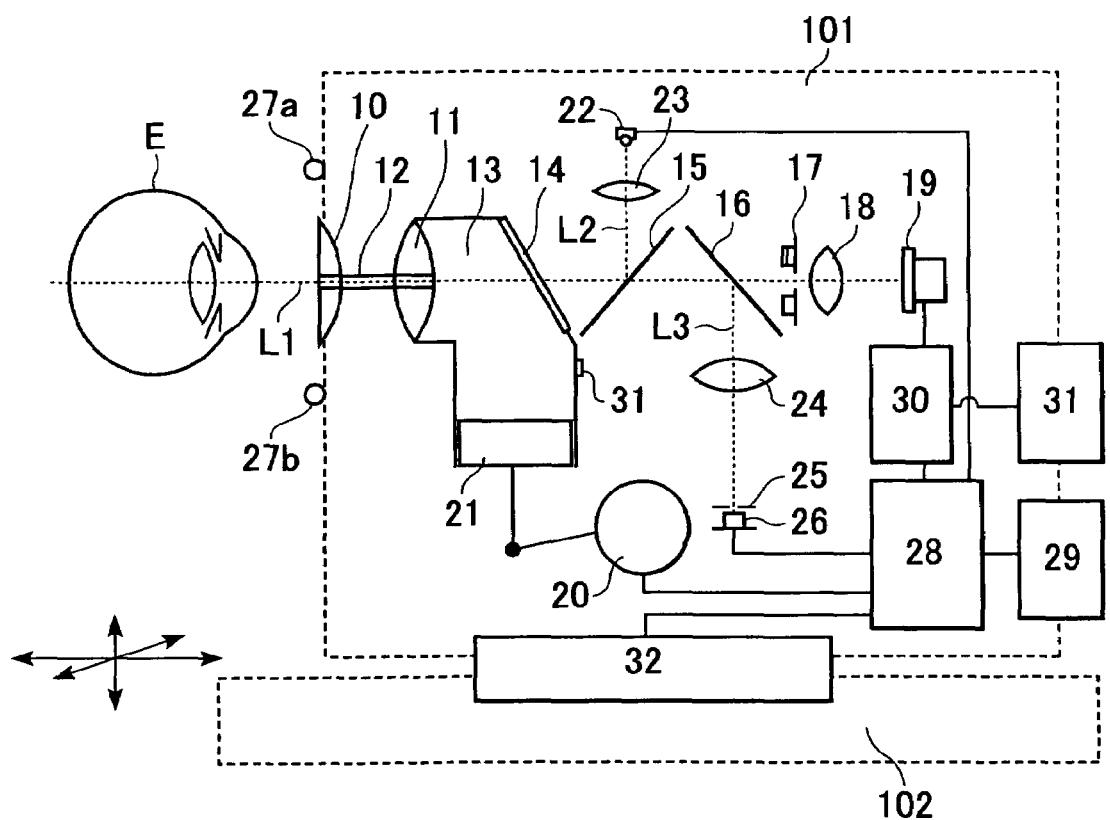
FIG. 1 is a drawing of an overall configuration of an embodiment according to the present invention.
Figure 2:
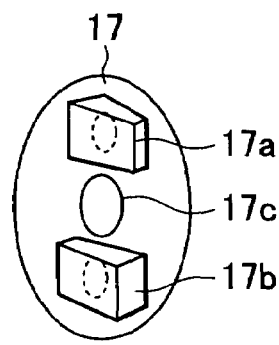
FIG. 2 is a detail view of an alignment diaphragm.

The present invention will be described in detail with reference to FIGS. 1 to 5B. FIG. 1 shows a configuration of a non-contact ophthalmotonometer incorporating the present invention; FIG. 2 shows a prism diaphragm 17 of the ophthalmotonometer in detail.

On an optical axis L1, opposing an examinee's eye E, there are provided an objective lens 10 having a nozzle 12 arranged on a central axis thereof, an objective lens 11, an air chamber 13, a viewing window 14, a dichroic mirror 15, a dichroic mirror 16, the prism diaphragm 17, an image-forming lens 18, and an image-pickup element 19 arranged in this order from the examinee's eye E. The dichroic mirror 16 has characteristics in that the light emitted from extraocular illuminating light-sources 27a and 27b, which will be described later, is transmitted while a large portion of the light from an LED light source 22 for use as both measurement and alignment is reflected. These elements, from the objective lens 10 to the image-pickup element 19, constitute a viewing system of an examinee's eye and an alignment detection system. The prism diaphragm 17, as shown in FIG. 2, is provided with three apertures, and there are prisms 17a and 17b disposed in the upper and lower apertures, respectively, for deflecting the luminous flux in left and right directions different from each other. The prism diaphragm 17 is also provided with a filter having spectral characteristic in that the light emitted from the extraocular illuminating light-sources 27a and 27b is absorbed while the light from the LED light source 22 for use as both measurement and alignment is transmitted.

Air contained in the air chamber 13 is compressed with a piston 21, which is raised with a solenoid 20, and is ejected toward the examinee's eye E via a nozzle 12 in a pulse-like pattern. The nozzle 12, the air chamber 13, the piston 21, and the solenoid 20 constitute an eye-pressurizing unit. There is also a pressure sensor 31 for monitoring the pressure in the air chamber 13 when the piston 21 is raised with the solenoid 20.

On the other hand, on an optical axis L2 in the reflecting direction of the dichroic mirror 15, there are arranged the LED light source 22 for use as both measurement and alignment and a projection lens 23. A narrow luminous flux projected from the LED light source 22 is illuminated on a cornea of the examinee's eye E after once focusing in the nozzle 12. The luminous flux reflected from the cornea is to be transmitted through the objective lenses 10 and 11 outside the nozzle 12. These elements constitute a measurement-light projection system and an alignment-indexing projection system.

Furthermore, on the optical axis L2, although not shown, a dichroic mirror, having characteristics in that visible light is reflected while infrared light is transmitted, is arranged at a slant of 45°. On an optical axis in the reflecting direction of this dichroic mirror, there is provided a fixation-lamp projection system for offering a fixation lamp for eye fixation to the examinee's eye.

Also, on an optical axis L3 in the reflecting direction of the dichroic mirror 16, there are arranged a lens 24, a pin-hole plate 25, and a light sensor 26. These elements, from the objective lenses 10 and 11 to the dichroic mirror 16, the lens 24, the pin-hole plate 25, and the light sensor 26, constitute a deflection-sensing received-ray system for sensing changes in the amount of light reflected from a cornea of an examinee's eye E when the cornea is deflected in a visual axial direction by the air ejected in a pulse pattern.

Moreover, at a position that is symmetric with respect to the optical axis of the objective lenses 10 and 11, anterior-eye-part illuminators 27a and 27b are arranged for illuminating an anterior eye part.

A measuring unit of the non-contact ophthalmotonometer is provided with determination processing unit 28 for controlling each part of the apparatus and for determining each control, and operating unit 29 for operating the apparatus by an operator.

The output of the image-pickup element 19 is transmitted to the determination processing means 28 via picture-signal processing means 30, which produces picture images to displaying means 31. Furthermore, there is provided driving means 32 for driving the measuring unit in three axial directions, which are the direction of the optical axis L1 and directions perpendicular to the optical axis L1 relative to the examinee's eye E. Referring to FIG. 1, a region surrounded by a dotted line located above the driving means 32 indicates a driving unit 101 while a region surrounded by a dotted line located below the driving means 32 indicates a fixed part 102, and these parts perform alignment operation through a driving mechanism (not shown). The determination processing means 28 according to the present invention will be described later in detail.

Next, operation of the present invention will be described. An illumination luminous flux emitted from the extraocular illuminating light-sources 27a and 27b illuminates the anterior eye part of the examinee's eye E. The illumination luminous flux, which is reflected and scattered from the anterior part of the examinee's eye, is substantially collimated by the objective lenses 10 and 11. Then it passes through the aperture at the center of the prism diaphragm 17 after transmitting the viewing window 14 and the dichroic mirrors 15 and 16 so as to be focused on the image-pickup element 19 with the image-forming lens 18. Then, the picture-signal processing means 30 performs binarization processing on the obtained anterior eye part image in an appropriate threshold value so as to provide it to the determination processing means 28. The determination processing means 28 obtains a pupilary center by detecting a pupil from the binary images, and it drives the driving unit 101 when the relative position of the optical axis L1 of the measuring unit and the pupil of the examinee's eye within a surface (x and y directions) perpendicular to the optical axis L1 is not within an allowable range, and it performs rough alignment so as to be fitted into the allowable range.

Upon substantial completion of the alignment of the examinee's eye E and the measuring unit within the surface perpendicular to the optical axis, the control means 32 turns on the LED light source 22. A luminous flux emitted from the LED light source 22 reaches the examinee's eye E so as to be reflected from the cornea of the examinee's eye E after once focusing in the nozzle 12 by the projection lens 23 and the dichroic mirror 15. After the luminous flux reflected from the cornea is condensed by the objective lenses 10 and 11 and passes through the viewing window 14, about 50% of the luminous flux penetrates the dichroic mirror 15 while part of the flux passes through the dichroic mirror 16. Then, the flux is divided into fluxes by the three apertures 17a, 17b, and 17c of the prism diaphragm 17, so as to be focused on the image-pickup element 19 by the image-forming lens 18. At this time, the luminous fluxes transmitted through the upper and lower apertures of the prism diaphragm 17 are deflected in back and forth directions perpendicular to the plane of the figure by the deflection prisms 17a and 17b, respectively, so that on the image-pickup element 19, the positional relationship between the corneal luminescent spot images divided into three from the LED light source 22 is changed by the relative position between the examinee's eye and the apparatus measuring unit, enabling the positional relationship between the examinee's eye and the apparatus to be obtained by detecting the positional relationship between the corneal luminescent spot images divided into three.

For example, if the distance between the examinee's eye and the apparatus measuring unit is larger than a predetermined distance, the corneal luminescent spot image on the image-pickup element 19 in the back direction perpendicular to the plane of the figure is moved downward while the corneal luminescent spot image in the forward direction is moved upward. In contrast, if the distance between the examinee's eye and the apparatus measuring unit is smaller than a predetermined distance, the corneal luminescent spot image on the image-pickup element 19 in the back direction perpendicular to the plane of the figure is moved upward while the corneal luminescent spot image in the forward direction is moved downward. Also, if there is positional displacement between the examinee's eye E and the apparatus measuring unit on the surface perpendicular to the optical axis, the positional relationship between the examinee's eye and the apparatus measuring unit can be obtained by detecting the center of gravity of the three corneal luminescent spot images or the position of the central corneal luminescent spot image.

Figure 3:
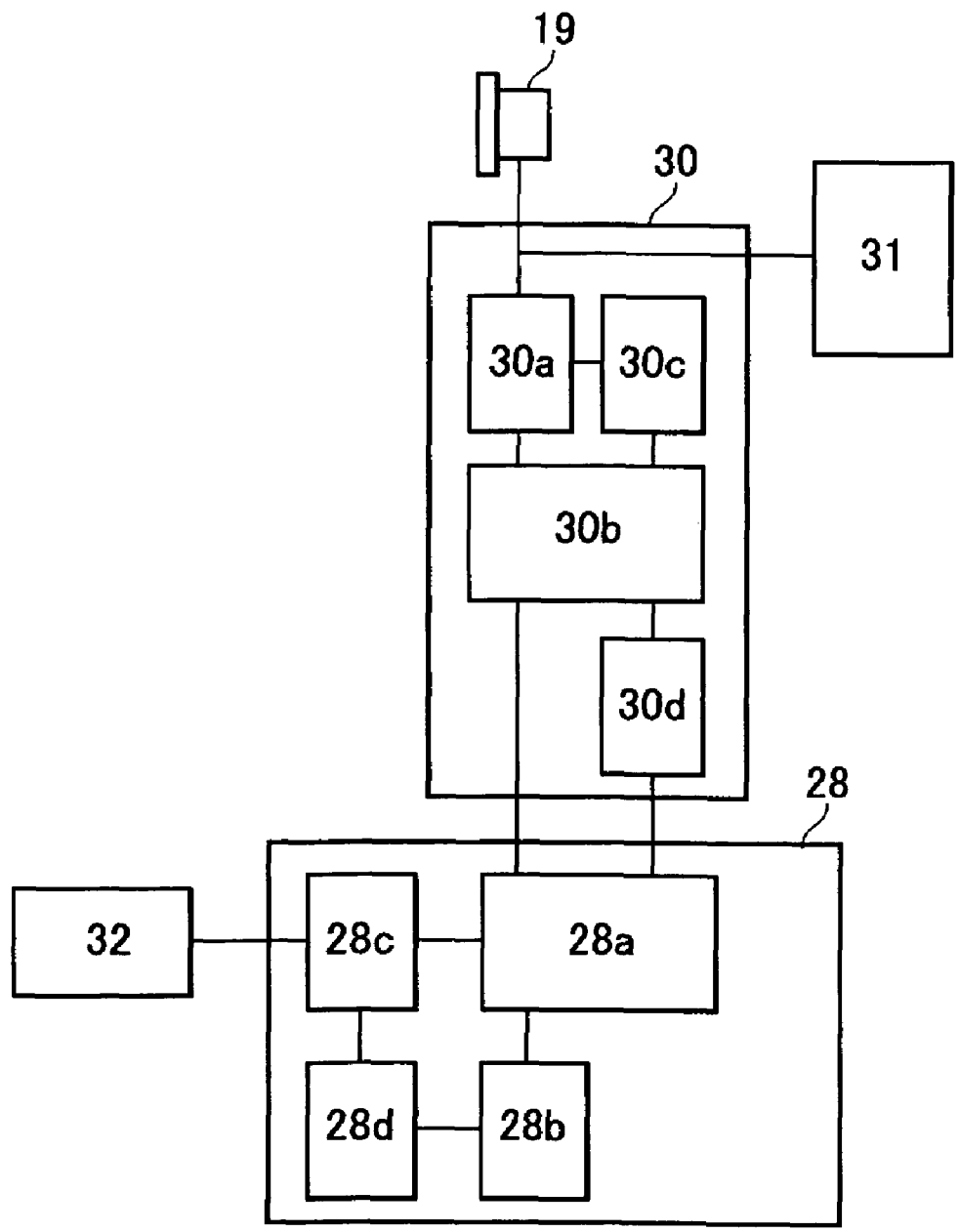
FIG. 3 is a detail view of an electrical processing section in FIG. 1.

A method of the above alignment according to the present invention will be described in detail. FIG. 3 is a drawing showing detailed structures of the image-pickup element 19, the picture-signal processing means 30, the displaying means 31, the determination processing means 28, and the driving means 32, which are shown in FIG. 1. However, part of the determination processing means 28 other than that relating to the present invention is omitted.

A picture signal produced from the image-pickup element 19 is entered in the picture-signal processing means 30. The produced picture signal has a route to be produced in directly displaying means 31 and a route to be entered in an A/D converter 30*a*. The data digitized by the A/D converter 30*a* is entered in a memory for images 30*b*. The succession of A/D control so far is performed by a timing control unit 30*c* commanded by the determination processing means 28 via a route (not shown). The data stored in the memory for images 30*b* is produced in the determination processing means 28 via two routes that are a direct route and performing binarization via an LUT (look up table) 30*d*.

The quality of the produced digital image data is determined by a decision unit 28*a*. The criteria for the quality decision will be described later. The quality decision results are stored in decision-result storing means 28*b*. The decision-result storing means 28*b* has a structure like a ring buffer in which an older buffer is overwritten if the number of buffers exceeds prepared numbers. That is, when the picture signal is incorporated (A/D conversion) at regular intervals, the newest data by an amount for a predetermined time is stored. The decision unit 28*a* simultaneously produces the digital image data to alignment analyzing unit 28*c*. The alignment analyzing unit 28*c* determines the next destination of the driving unit 101 after analyzing the image data so as to dictate a driving command to the driving means 32 while adjusting the speed.

Figure 4A:
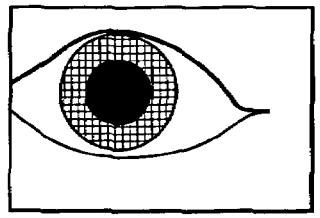
FIGS. 4A to 4C are pictures obtained during rough alignment.
Figure 4B:
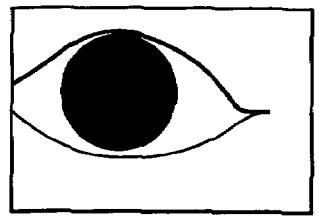
Figure 4C:
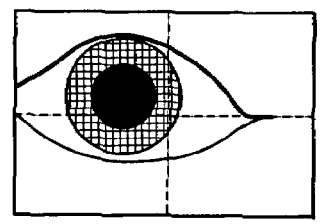

Next, a decision example of the rough alignment mentioned above will be described. FIG. 4A shows an anterior eye part image obtained by the image-pickup element 19. The LUT 30*d*, as shown in FIG. 4B, performs the binarization processing on this image so as to provide it to the decision unit 28*a*. The decision unit 28*a* obtains the area of a pupil from this image and performs circular approximation thereon. If the pupil area is reduced, it is smaller than a predetermined area, or the pupil is deviated from a circular shape, the quality is determined to be negative so as to be recorded in the decision-result storing means 28*b*. By contrast, images with no problem are determined to be positive and recorded. The images determined to be positive are produced to the alignment analyzing unit 28*c*. The alignment analyzing unit 28*c* obtains the distance between the center of the image picking-up unit shown in the intersecting point of the dotted lines in FIG. 4C, so as to set up the next driving position in the driving means 32. In such a manner, the quality decision during the rough alignment is made based upon changes in a pupilary eye part such as a falling pupil and scintillation from the obtained binary images.

Figure 5A:
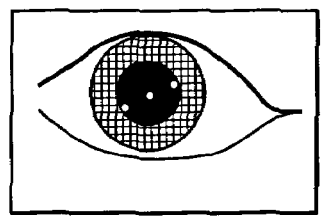
FIGS. 5A and 5B are pictures obtained during fine alignment.
Figure 5B:
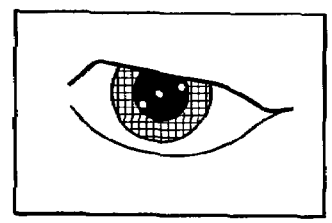

Next, an example of this decision method will be described with respect to fine alignment performed after the above-mentioned LED light source 22 is turned on. FIG. 5A is a drawing showing an alignment index due to the LED light source 22 focused on the image-pickup element 19, wherein luminous fluxes led by the deflecting prisms 17*a* and 17*b* are located on the left and right of three-point luminous spots, respectively. FIG. 5B shows the case where the upper luminous flux is covered by cilia, so that the left luminous spot is darkened. The decision unit 28*a*, in such a manner, detects dispersion in the light amount of the luminous spots, or it detects a falling pupil and scintillation by checking whether the three-point luminous spots are visible. Also, it is detectable that fixation is unstable by the disparity between the center of the three-point luminous spots and the pupil center and that the face is moved by the disparity of the entire pupil. The decision results obtained here are similarly stored in the decision-result storing means 28*b*, wherein the results determined to be positive are produced to the alignment analyzing unit 28*c* so as to dictate a driving command to the driving means 32 in the same way.

Next, a count unit 28*d* will be described. As described above, the decision results produced by the decision unit 28*a* are stored in the decision-result storing means 28*b* by the amount for a predetermined time. The count unit 28*d* consistently compares the stored data with a predetermined condition. That is, the count unit 28*d* is monitoring whether NG or OK for the condition such as to determine NG if for 20 decision results, ten or more negative decision results are counted, or the negative decisions are repeated continuously for five times. In the case of NG, the alignment interruption is commanded to the alignment analyzing unit 28*c*. The stoppage is thereby commanded to the driving unit 101 from the driving means 32. The count unit 28*d* may also have an alarming unit such as a buzzer (not shown) so as to issue a warning according to the NG decision at this timing.

Awareness of an alignment enables an operator to perform an appropriate patient care operation such as to raise an eyelid, fix the head, open an eye wider, or allow the patient to have a rest for a while.

As described above, by quantitatively determining a state of an examinee's eye, the alignment interruption and the appropriate patient care operation are enabled without causing an excessive degree of fear to an examinee who is fearful of the alignment operation.

Next, a control method related to the second object of the present invention will be described. As described above, even in the case where the state of an examinee's eye is not so good so that an interruption and a warning are issued with an NG decision, the picture incorporation, the determination, and the storing of the determined result are continued, wherein the count unit 28d transferring the result to the interruption or warning state estimates the determined results under a new condition. For example, if for 20 decision results, 15 positive decision results are counted, or the positive decisions are repeated continuously for 10 times, it is determined that the abovementioned appropriate patient care operation be performed, so that a command to restart the driving is issued to the alignment analyzing unit 28c. The controlling by the driving means 32 is thereby restarted so as to restart driving the driving unit 101. Wherein if the alignment analyzing unit 28c recognizes that the alignment state extends within a predetermined acceptable limit so as to determine the alignment completion, the alignment is transferred to the measurement operation.

According to the embodiment, the acceptable limit for recognizing the alignment completion is constant. Alternatively, a method may be incorporated, in which the alignment acceptable limit is variable corresponding to the result from the count unit 28d. In this case, processing is performed such that if a number of negative decision results are counted, the acceptable limit is extended while if the negative decision result is scarcely counted, the acceptable limit is narrowed. For example, if for 20 decision results, ten or more negative decision results are counted, the alignment interruption or warning is commanded as described above while if for 20 decision results, five or more negative decision results are counted, the processing to extend the acceptable limit is performed. Thereby, on an examinee with excellent eye-fixation, more precise measurement can be performed, while on an examinee with slightly weak eye-fixation although the alignment interruption or warning is not commanded, the alignment can be more rapidly completed.

In the measurement operation, as shown in FIG. 1, the determination processing means 28 drives the solenoid 20 so as to eject air in a pulse pattern to a cornea of the examinee's eye E from the nozzle 12. Then, the cornea of the examinee's eye E is deformed corresponding to the intensity of the sprayed airflow, and the state of the deformation can be detected by the light sensor 26. The determination processing means 28 calculates the intraocular pressure of the examinee based on the output of the light sensor 26 and the output signal of the pressure sensor 31. By the configuration described above, a non-contact ophthalmotonometer can be constructed in that the alignment operation is restarted by quantitatively determining that a proper patient care operation has been performed.

The present invention has been described by incorporating the non-contact ophthalmotonometer thereto; alternatively, another ophthalmologic apparatus may have the same advantages with the same control method as long as the apparatus has an auto-alignment mechanism.

Also, in the above description, the count unit 28d compares the result with a constant condition regardless of the alignment, rough or fine. However, if the comparison condition is changed, such as to determine NG if for 20 decision results, five or more negative decision results are counted during the rough alignment, and to determine NG if for 20 decision results, ten or more negative decision results are counted during fine alignment, an examinee having excessive fear during the rough alignment, in which an objective lens is not yet spaced from the eye, can be discovered in earlier stages. Also, even in an apparatus having no distinct segmentation between the rough and fine alignments, by providing a measuring unit for measuring the positional relationship between the driving unit 101 and the fixed part 102 so as to change the comparison condition corresponding to the distance to the examinee's eye, the same advantages are obtained.

The condition with which the count unit 28d compares is exemplified as the already fixed condition; however, the operability is obviously improved if an operator can set a comparison reference value from the operating unit 29.

The luminous spots for the fine alignment have been described referring to the optical drawing in FIG. 1. Alternatively, the prism diaphragm 17 can be attached in a state rotated by an angle of 90° relative to the sate shown in FIGS. 1 and 2. In this case, in the three-point luminous spots shown in FIG. 5A and having proper alignment, the three points are vertically aligned, so that if the falling pupil shown in FIG. 5B is produced, the upper luminous spot is projected on the pupil so as to be significantly difficult to detect. This state may also be reflected in the quality decision during the fine alignment described above.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. An ophthalmologic apparatus comprising:
   alignment driving means for aligning an examinee's eye;
   detecting means for detecting an alignment state of the examinee's eye; and
   alignment controlling means for controlling the alignment driving means based on a result detected by the detecting means,
   wherein the alignment controlling means comprises determining means for determining a quality of the detected result and counting means for counting outputs from the determining means within a predetermined period of time, and the alignment controlling means performs the control of the alignment driving means based on the output of the counting means.

2. An apparatus according to claim 1, wherein the alignment controlling means performs interruption processing for interrupting the driving of the alignment driving means based on the output of the counting means.

3. An apparatus according to claim 1 or 2, wherein the detecting means comprises an acceptable limit for recognizing the alignment completion, and changes the acceptable limit based on the output of the counting means.

4. An apparatus according to claim 1 or 2, wherein the counting means counts at least one of positive and negative decisions determined by the determining means.

5. An apparatus according to claim 1 or 2, wherein the counting means comprises comparing means for comparing the output from the counting means with a predetermined reference value and inputting means for inputting the reference value.

6. An apparatus according to claim 1 or 2, further comprising position detecting means for detecting positional information of the examinee's eye,
   wherein the counting means comprises comparing means for comparing the output from the counting means with a predetermined reference value so as to change the reference value based on the output from the position detecting means.

7. An apparatus according to claim 1 or 2, wherein the alignment control is further restarted based on the output from the counting means.

8. An apparatus according to claim 1 or 2, wherein the counting means respectively counts positive and negative decisions determined by the determining means, so that the interruption processing is performed corresponding to the number of the negative decisions while restarting control is performed corresponding to the number of the positive decisions.

* * * * *